(12) United States Patent
Miyamoto et al.

(10) Patent No.: US 9,161,744 B2
(45) Date of Patent: *Oct. 20, 2015

(54) TREATMENT TOOL FOR ENDOSCOPE

(75) Inventors: Manabu Miyamoto, Tokyo (JP); Keita Suzuki, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 1322 days.

This patent is subject to a terminal disclaimer.

(21) Appl. No.: 12/027,515

(22) Filed: Feb. 7, 2008

(65) Prior Publication Data

US 2008/0194910 A1 Aug. 14, 2008

(30) Foreign Application Priority Data

Feb. 8, 2007 (JP) .................................. 2007-029052
Apr. 27, 2007 (JP) .................................. 2007-119384

(51) Int. Cl.
*A61B 10/06* (2006.01)
*A61B 17/29* (2006.01)

(52) U.S. Cl.
CPC ......... *A61B 10/06* (2013.01); *A61B 2017/2902* (2013.01); *A61B 2017/293* (2013.01); *A61B 2017/2905* (2013.01); *A61B 2017/2929* (2013.01)

(58) Field of Classification Search
CPC ............... A61B 2017/2901; A61B 2017/2903; A61B 2017/2912; A61B 2017/2924; A61B 10/06; A61B 2017/2929; A61B 2017/293; A61B 2017/2905; A61B 2017/2902; A61B 17/00234; A61B 17/29; A61B 19/22; A61B 1/018; A61B 18/085; A61B 18/142; A61B 18/1445; A61B 18/1447

USPC ................ 606/205, 207, 208; 600/104
See application file for complete search history.

(56) References Cited

U.S. PATENT DOCUMENTS 4,632,110 A * 12/1986 Sanagi ........................... 606/207
4,817,630 A * 4/1989 Schintgen et al. ............ 600/564
4,932,419 A * 6/1990 de Toledo .................... 600/585

(Continued)

FOREIGN PATENT DOCUMENTS

DE   88 08 285 U1   9/1988
EP    1 454 588 A2   9/2004

(Continued)

OTHER PUBLICATIONS

European Office Action dated Jan. 22, 2010.

(Continued)

*Primary Examiner* — David Eastwood
*Assistant Examiner* — Martin T Ton
(74) *Attorney, Agent, or Firm* — Scully, Scott, Murphy & Presser, PC

(57) ABSTRACT

A treatment tool of an endoscope including: a movable tip end portion that performs a treatment on a living body; a flexible first coil sheath into which a wire is spirally wound; a flexible second coil sheath into which a wire is spirally wound and which is concentrically fitted onto or into the first coil sheath; a flexible operation wire that is formed into an elongated thin shape, a tip end thereof being connected to the movable tip end portion, and the operation wire being movably inserted into the first coil sheath; and an operation portion for advancing and retracting the operation wire, in which a tip end of the second coil sheath is fixed to the movable tip end and a base end thereof is fixed to the operation portion.

7 Claims, 18 Drawing Sheets

(56) References Cited

U.S. PATENT DOCUMENTS

| | | | |
|---|---|---|---|
| 4,951,677 A | 8/1990 | Crowley et al. | |
| 5,052,404 A * | 10/1991 | Hodgson | 600/585 |
| 5,108,411 A * | 4/1992 | McKenzie | 606/159 |
| 5,165,421 A * | 11/1992 | Fleischhacker et al. | 600/585 |
| 5,251,640 A * | 10/1993 | Osborne | 600/585 |
| 5,306,252 A * | 4/1994 | Yutori et al. | 600/585 |
| 5,368,035 A | 11/1994 | Hamm et al. | |
| 5,373,619 A | 12/1994 | Fleischhacker et al. | |
| 5,406,951 A | 4/1995 | ten Hoff et al. | |
| 5,437,282 A | 8/1995 | Koger et al. | |
| 5,438,997 A | 8/1995 | Sieben et al. | |
| 5,482,054 A | 1/1996 | Slater et al. | |
| 5,501,694 A * | 3/1996 | Ressemann et al. | 606/159 |
| 5,507,296 A * | 4/1996 | Bales et al. | 600/564 |
| 5,524,630 A | 6/1996 | Crowley | |
| 5,609,285 A * | 3/1997 | Grant et al. | 227/179.1 |
| 5,649,955 A * | 7/1997 | Hashimoto et al. | 606/205 |
| 5,678,296 A * | 10/1997 | Fleischhacker et al. | 29/451 |
| 5,796,044 A | 8/1998 | Cobian et al. | |
| 5,803,812 A * | 9/1998 | Kakiuchi et al. | 464/58 |
| 5,810,887 A * | 9/1998 | Accorti et al. | 607/122 |
| 5,816,923 A * | 10/1998 | Milo et al. | 464/58 |
| 5,893,885 A | 4/1999 | Webster, Jr. | |
| 6,015,381 A * | 1/2000 | Ouchi | 600/104 |
| 6,027,460 A * | 2/2000 | Shturman | 600/585 |
| 6,027,522 A * | 2/2000 | Palmer | 606/205 |
| 6,078,830 A | 6/2000 | Levin et al. | |
| 6,129,683 A * | 10/2000 | Sutton et al. | 600/564 |
| 6,210,395 B1 * | 4/2001 | Fleischhacker et al. | 604/526 |
| 6,273,860 B1 * | 8/2001 | Kostylev et al. | 600/564 |
| 6,344,037 B1 * | 2/2002 | Suorsa et al. | 604/528 |
| 6,364,846 B1 | 4/2002 | Nakamura | |
| 6,409,727 B1 | 6/2002 | Bales et al. | |
| 6,419,644 B1 | 7/2002 | White et al. | |
| 6,443,909 B1 * | 9/2002 | Ouchi | 600/562 |
| 6,522,930 B1 | 2/2003 | Schaer et al. | |
| 6,792,663 B2 * | 9/2004 | Krzyzanowski | 29/434 |
| 6,818,001 B2 * | 11/2004 | Wulfman et al. | 606/159 |
| 6,881,194 B2 | 4/2005 | Miyata et al. | |
| 7,117,703 B2 * | 10/2006 | Kato et al. | 72/135 |
| 7,588,545 B2 * | 9/2009 | Cohen et al. | 600/564 |
| 7,815,658 B2 * | 10/2010 | Murakami | 606/169 |
| 2001/0052721 A1 * | 12/2001 | Tanaka | 297/367 |
| 2002/0062124 A1 | 5/2002 | Keane | |
| 2002/0177772 A1 | 11/2002 | Altman et al. | |
| 2003/0139689 A1 | 7/2003 | Shturman et al. | |
| 2003/0139750 A1 * | 7/2003 | Shinozuka et al. | 606/113 |
| 2003/0236549 A1 * | 12/2003 | Bonadio et al. | 606/205 |
| 2004/0068291 A1 * | 4/2004 | Suzuki | 606/205 |
| 2004/0243108 A1 | 12/2004 | Suzuki | |
| 2005/0004432 A1 * | 1/2005 | Suzuki et al. | 600/146 |
| 2006/0229644 A1 * | 10/2006 | Kortenbach | 606/153 |
| 2007/0255311 A1 * | 11/2007 | Hiraoka | 606/205 |
| 2008/0195143 A1 | 8/2008 | Suzuki | |
| 2010/0228150 A1 * | 9/2010 | Zimmerman et al. | 600/585 |

FOREIGN PATENT DOCUMENTS

| | | |
|---|---|---|
| EP | 1 491 153 A1 | 12/2004 |
| JP | 55-109501 | 7/1980 |
| JP | 63-154173 | 6/1988 |
| JP | 10-507959 | 8/1998 |
| JP | 2000-229084 | 8/2000 |
| JP | 2000-333970 | 12/2000 |
| JP | 2002-102245 | 4/2002 |
| JP | 2004-261463 A | 9/2004 |
| JP | 2005-058344 | 3/2005 |
| JP | 4526544 B2 | 8/2010 |
| WO | WO 96/36289 A1 | 11/1996 |
| WO | 97/07835 | 3/1997 |
| WO | WO 2006/114952 A1 | 11/2006 |

OTHER PUBLICATIONS

U.S. Office Action for related U.S. Appl. No. 11/471,051, filed Oct. 12, 2010.

U.S. Office Action for related U.S. Appl. No. 12/026,881, filed Sep. 2, 2010.

Partial European Search Report dated Dec. 1, 2006 in connection with corresponding European Patent Application No. 06012569.7.

Japanese Office Action (Notice of Allowance) dated May 25, 2010 together with an English language translation.

Japanese Office Action dated Mar. 15, 2011.

U.S. Office Action of corresponding U.S. Appl. No. 12/026,881 dated Apr. 13, 2011.

Extended European Search Report dated Dec. 3, 2010 received in related U.S. Appl. No. 12/026,881.

Abstract only of Japanese Patent Application No. JP 2008-194068 dated Aug. 28, 2008.

Japanese Office Action dated Jan. 31, 2012 from corresponding Japanese Patent Application No. JP 2007-119384.

* cited by examiner

TREATMENT TOOL FOR ENDOSCOPE

BACKGROUND OF THE INVENTION

1. Field of the Invention

The present invention relates to a treatment tool for an endoscope.

Priority is claimed on Japanese Patent Application No. 2007-029052, filed on Feb. 8, 2007, and Japanese Patent Application No. 2007-119384, filed on Apr. 27, 2007, the contents of which are incorporated herein by reference.

2. Description of Related Art

A treatment tool for an endoscope, such as grasping forceps, for use together with a flexible endoscope, is provided with a coil sheath into which a wire is wound. It is inserted into a body cavity via a treatment tool insertion channel of the endoscope. In this state, in order to revolve the tip end portion of the treatment tool for the endoscope about the axis, an operation portion on the proximal side of the treatment tool for the endoscope is rotated in most cases. Accordingly, treatment tools are known in which a multi wire coil sheath with high rotation transmissibility is arranged so as to improve the rotation following capability of the movable tip end portion.

Here, in the case of a treatment tool such as forceps that is opened and closed by pulling an operation wire from the operation portion, a compression force is loaded in the axis direction of the coil sheath in accordance with the opening and closing. At this time, a multi wire coil sheath into which a plurality of wires are wound has a higher rotation transmissibility compared to a single wire coil sheath into which a single wire is wound, but is more likely to be compressed in the axis direction. As a result, the coil sheath is compressed in the axis direction, which decreases the axial force to be transmitted to the tip end portion. This prevents sufficient treatment, leading to a complicated manipulation. Consequently, there is proposed a treatment tool in which single wire coil sheaths are arranged in multiple layers (for example, see Japanese Unexamined Patent Publication, First Publication No. 2000-229084).

SUMMARY OF THE INVENTION

A treatment tool of an endoscope according to the first aspect of the present invention includes: a movable tip end portion that performs a treatment on a living body; a flexible first coil sheath into which a wire is spirally wound; a flexible second coil sheath into which a wire is spirally wound and which is concentrically fitted onto or into the first coil sheath; a flexible operation wire that is formed into an elongated thin shape, a tip end thereof being connected to the movable tip end portion, and the operation wire being movably inserted into the first coil sheath; and an operation portion for advancing and retracting the operation wire, in which a tip end of the second coil sheath is fixed to the movable tip end and a base end thereof is fixed to the operation portion.

Furthermore, in the treatment tool for an endoscope according to the present invention, it is preferable that a tip end of the first coil sheath be rotatably connected to the movable tip end portion and that a base end thereof be rotatable connected to the operation portion.

Furthermore, in the treatment tool for an endoscope according to the present invention, it is preferable that at least either one of the wire of the first coil sheath and the wire of the second coil sheath have a substantially rectangular cross section.

Furthermore, in the treatment tool for an endoscope according to the present invention, it is preferable that the winding direction of the wire of the first coil sheath coincide with the winding direction of the wire of the second coil sheath.

Furthermore, in the treatment tool for an endoscope according to the present invention, it is preferable that the winding direction of the wire of the first coil sheath and a winding direction of the wire of the second coil sheath be opposite to each other.

A treatment tool of an endoscope according to the second aspect of the present invention includes: a movable tip end portion having a movable part that performs a treatment on a living body; a flexible operation wire that is formed into an elongated thin shape, a tip end thereof being connected to the movable part of the movable tip end portion; an advancing/retracting operation portion for advancing and retracting the operation wire; a flexible first sheath which receives axial force generated between the movable tip end portion and the advancing/retracting operation portion in the axis direction at the time of advancing and retracting the operation wire by operating the advancing/retracting operation portion; a flexible second sheath disposed coaxially with the first sheath and connected to the movable tip end portion in the rotation direction about the axis; and a rotation operation portion for rotating the second sheath about the axis.

DETAILED DESCRIPTION OF THE INVENTION

Figure 1:
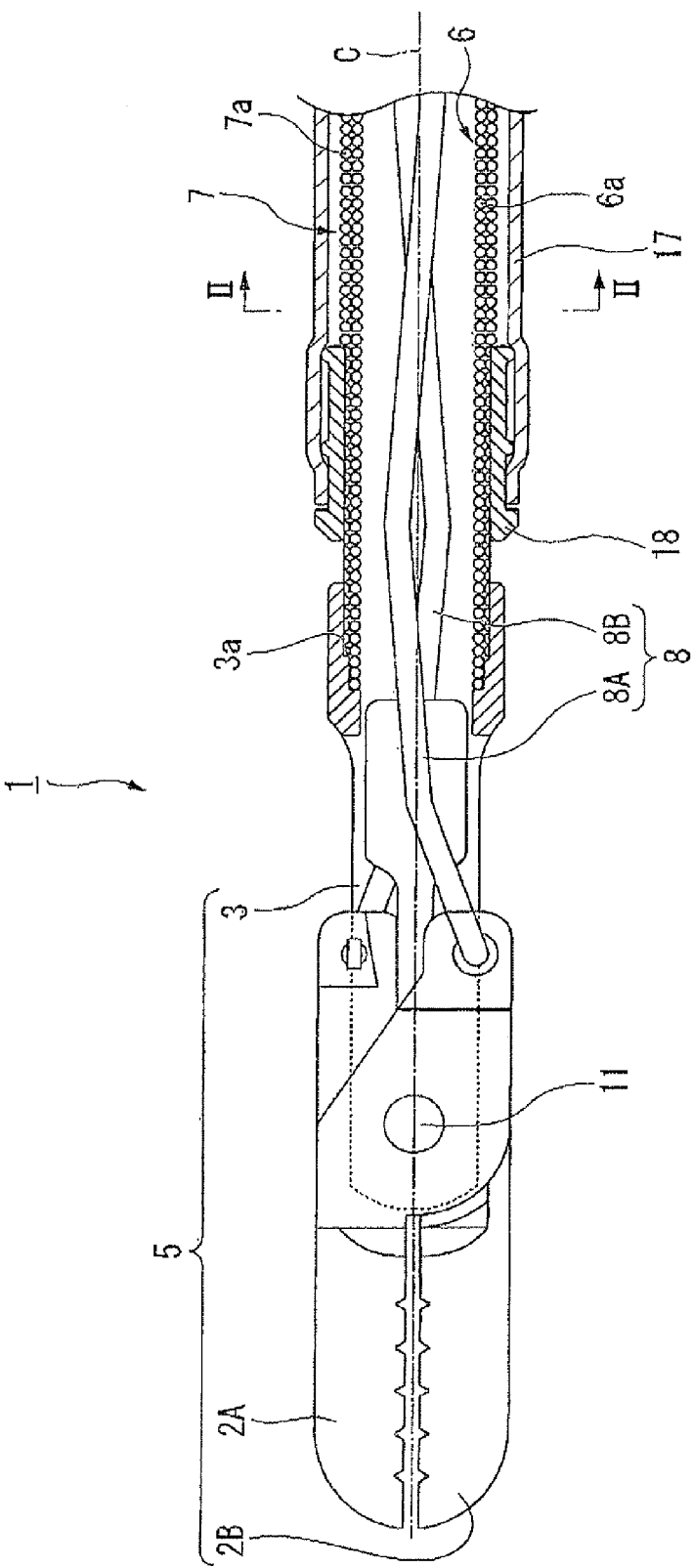
FIG. 1 is a cross sectional view showing a tip end side of forceps for an endoscope according to a first embodiment of the present invention.
Figure 2:
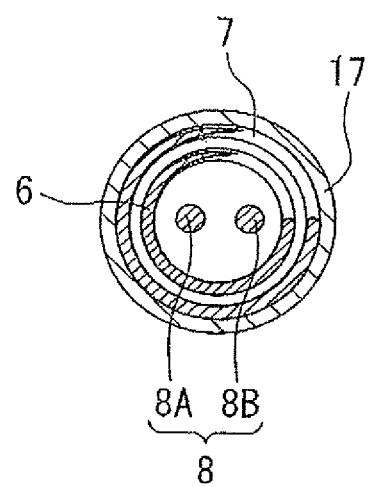
FIG. 2 is a cross sectional view taken along the line II-II in FIG. 1.
Figure 3:
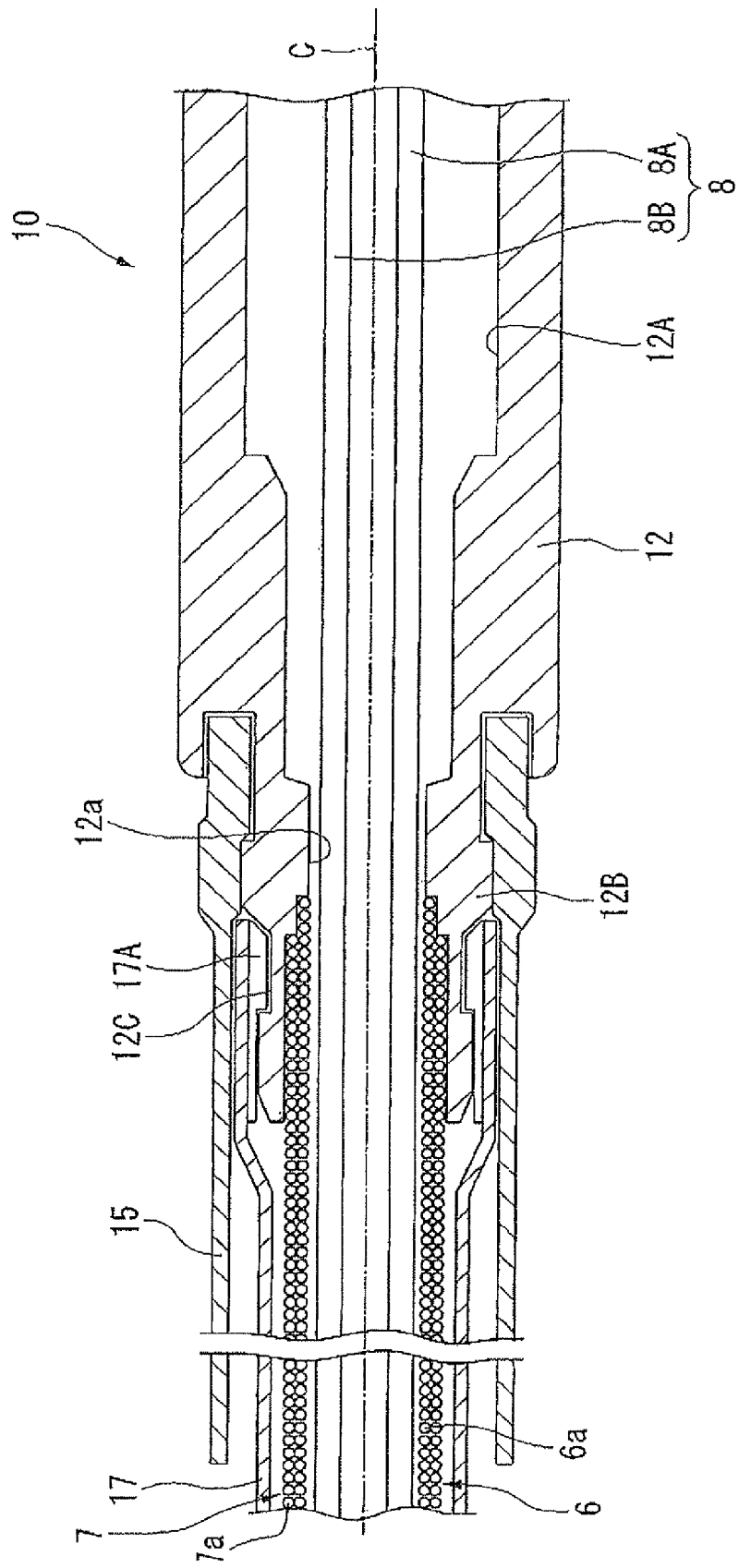
FIG. 3 is a cross sectional view showing a base end side of the forceps for an endoscope according to the first embodiment of the present invention.
Figure 4:
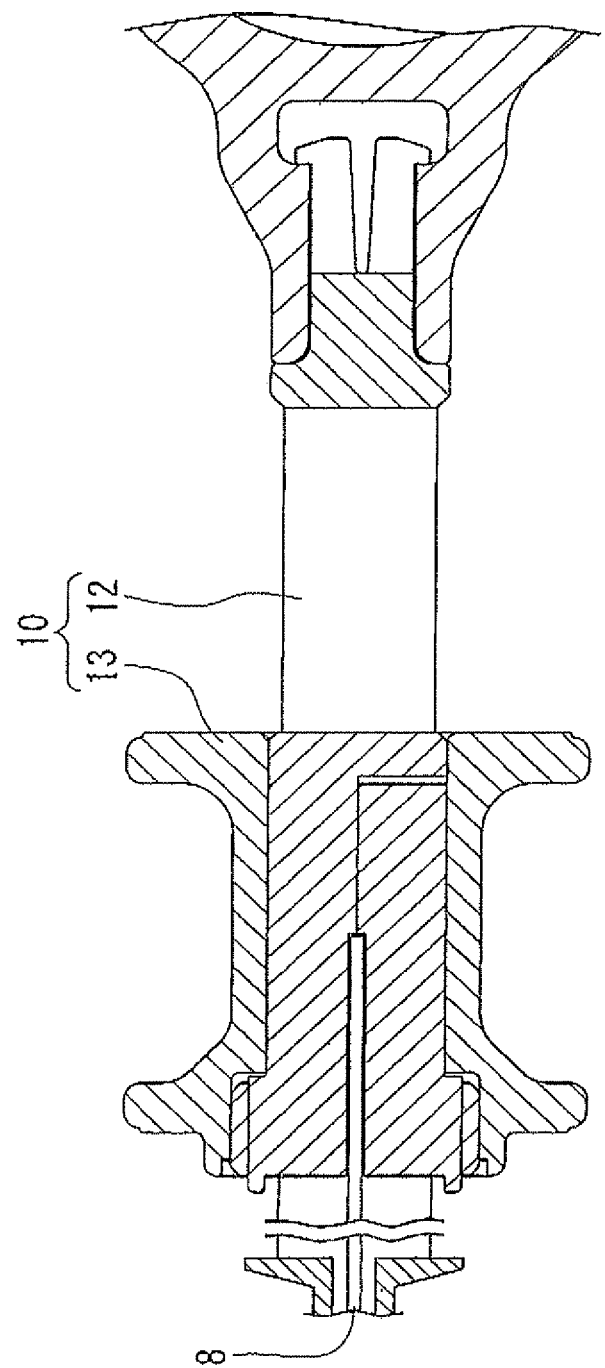
FIG. 4 is a part of a cross sectional view showing an operation portion of the forceps for an endoscope according to the first embodiment of the present invention.

A first embodiment according to the present invention will be described with reference to FIG. 1 to FIG. 4.

Forceps for an endoscope (a treatment tool for an endoscope) 1 according to the present invention includes: a movable tip end portion 5 with a pair of forceps arms 2A and 2B (movable part), and with a tip end cover 3 for performing a treatment on a living body; a flexible first coil sheath 6 into which a single wire 6a is spirally wound; a flexible second coil sheath 7 into which a plurality of wires 7a are spirally wound in the same direction and which is concentrically fitted onto the first coil sheath 6; a flexible operation wire 8 that is formed into an elongated thin shape, a tip end thereof being connected to the movable tip end portion 5, and the operation wire 8 being movably inserted into the first coil sheath 6; and an operation portion 10 for advancing and retracting the operation wire 8.

The tip end cover 3 is formed in a substantially cylindrical shape. On the tip end side thereof, there is rotatably provided a pivot support axis 11 for pivotally supporting the pair of forceps arms 2A and 2B. In an inner circumferential surface on the base end side of the tip end cover 3, there is provided a step 3a with which tip end portions of the first coil sheath 6 and the second coil sheath 7 are fitted respectively.

The operation portion 10 includes: a stick-like operation portion main unit 12 that extends in a central axis line C direction; and a slider 13 arranged in a freely advancing and retracting manner in the central axis line C direction with respect to the operation portion main unit 12. The operation portion 10 serves both as an advancing/retracting operation portion and a rotation operation portion. In the operation portion main unit 12, there is provided a slit 12A through which the operation wire 8 is inserted in the central axis line C direction. On the tip end side of the operation portion main unit 12, there is provided a protrusion portion 12B to whose inner circumferential surface the base ends of the first coil sheath 6 and the second coil sheath 7 are connected. In the protrusion portion 12B, there is provided a through-hole 12a which is communicated with the slit 12A. The outside of the protrusion portion 12B is covered with a breakage prevention portion 15 for protecting a connection portion with the first coil sheath 6 and the second coil sheath 7.

The first coil sheath 6 has its tip end side fixedly connected with the tip end cover 3, and has its base end fixedly fitted with the inner circumferential surface of the through-hole 12a of the protrusion portion 12B of the operation portion main unit 12. The first coil sheath 6 is formed of the single wire 6a spirally wound, and hence is formed as a single wire coil. Consequently, the first coil sheath 6 is unlikely to be deformed even if it is compressed in the central axis line C direction, and thus has to have a substantially circular cross section.

The second coil sheath 7 is fixedly connected with the tip end cover 3 around its outer circumferential surface on the tip end side in a state where a part of the wire 7a is cut away, and has its base end fixedly fitted with the inner circumferential surface of the through-hole 12a of the protrusion portion 12B of the operation portion main unit 12. The second coil sheath 7 is formed of the plurality of wires 7a spirally wound, and hence is formed as a multi wire coil, which makes it easy to transmit rotation torque about the central axis line C. The wires 7a are wound in the same direction as the wire 6a of the first coil sheath 6, and are for example, made of stainless steel and formed to have a substantially circular cross section.

On the tip end side of the second coil sheath 7, there is fitted a connection member 18 onto which a tip end of an insulating tube 17 is fitted. On a base end of the insulating tube 17, there is provided a tube side engaging protrusion portion 17A that is rotatably engaged with an operation portion side engaging recess portion 12C provided in the protrusion portion 12B of the operation portion main unit 12.

The operation wire 8 includes: a first wire 8A rotatably connected with the base end of the forceps arm 2A; and a second wire 8B rotatably connected with the base end of the forceps arm 2B. Both wires 8A and 8B are arranged through the through-hole 12a of the operation portion main unit 12, and extend through the slit 12A. Base ends thereof are connected with the slider 13. The tip end sides of the first wire 8A and the second wire 8B are bent so as to be spaced away from the central axis line C.

Next is a description of the operation of the forceps for an endoscope 1 according to the present embodiment.

The forceps for an endoscope 1 is inserted into a treatment tool channel of an endoscope (not shown in the figure) previously inserted into a body cavity, and the movable tip end portion 5 is protruded from the tip end of the endoscope to perform a treatment.

At this time, if the opening/closing direction of the pair of forceps arms 2A and 2B is different from the direction in which the affected area (not shown in the figure) is to be gripped, it is necessary to adjust the forceps for an endoscope 1 so that these two directions coincide. Therefore, the insulating tube 17 is gripped and the operation portion 10 is rotated about the central axis line C to make the opening/closing direction of the pair of forceps arms 2A and 2B coincide with the direction in which the affected area should be gripped.

At this time, the second coil sheath 7 is constructed as described above. Consequently, when the operation portion 10 is rotated by a predetermined angle, rotation torque is transmitted to the second coil sheath 7 in a manner following the rotated angle. This rotation torque is then transmitted to the movable tip end portion 5, thereby rotating the movable tip end portion 5 about the central axis line C by the predetermined angle. Note that, at this time, the first coil sheath 6 is also rotated accompanyingly.

After the opening/closing direction of the pair of forceps arms 2A and 2B is made to coincide with the direction in which the affected area should be gripped, the slider 13 is moved to the base end side with respect to the operation portion main unit 12 to move the operation wire 8 to the tip end side with respect to the first coil sheath 6 and the second coil sheath 7. At this time, the tip end sides of the first wire 8A and the second wire 8B are spaced away from the central axis line C. Therefore, the pair of forceps arms 2A and 2B is rotated about the pivot support axis 11 to bring the pair of forceps arms 2A and 2B into an open state.

In this state, the slider 13 is moved to the base end side with respect to the operation portion main unit 12 to move the operation wire 8 to the base end side with respect to the first coil sheath 6 and the second coil sheath 7. At this time, the respective tip ends of the first coil sheath 6 and the second coil sheath 7, and the respective base ends thereof are fixed. Therefore, the first coil sheath 6 and the second coil sheath 7 are compressed in the central axis line C direction in accordance with the movement of the operation wire 8.

Here, the first coil sheath 6 is constructed as described above. Therefore, even if the second coil sheath 7 is going to be compressed more than necessary, the second coil sheath 7 is not compressed more than necessary because the first coil sheath 6 has high compression resistance. Consequently, axial force resulting from the movement of the operation wire 8 with respect to the first coil sheath 6 and the second coil sheath 7 is transmitted to the pair of forceps arms 2A and 2B while being prevented from being used for compressing the first coil sheath 6 and the second coil sheath 7. In this manner, the pair of forceps arms 2A and 2B is rotated about the pivot support axis 11 to be closed, to thereby grip the affected area with necessary gripping force.

According to this forceps for an endoscope 1, in order to operate the movable tip end portion 5, advancing/retracting operation is performed on the slider 13 of the operation portion 10 with respect to the operation portion main unit 12 to move the operation wire 8 in the axis direction with respect to the first coil sheath 6. At this time, even if a compression force is loaded on the second coil sheath 7 whose tip end and base end are fixed, compression on the second coil sheath 7 is relaxed by the first coil sheath 6 with high compression resistance due to the single wire 6a spirally wound, thereby allowing a sufficient control force to be favorably transmitted to the movable tip end portion 5.

Furthermore, the second coil sheath 7 with high rotation transmissibility due to the plurality of wires 7a spirally wound in the same direction is less likely to be twisted than the first coil sheath 6. Therefore, even if the first sheath 6 is going to be twisted when the operation portion 10 is rotated about the central axis line C to rotate the movable tip end portion 5, it is possible to obtain high rotation following capability. In addition, because the outer diameter of the second coil sheath 7 is larger than that of the first coil sheath 6, it is possible to make the transmissibility of the rotation torque in the second coil sheath 7 higher. Consequently, it is possible to improve both the rotation operability and workability of the movable tip end portion 5 and to facilitate a manipulation.

Figure 5:
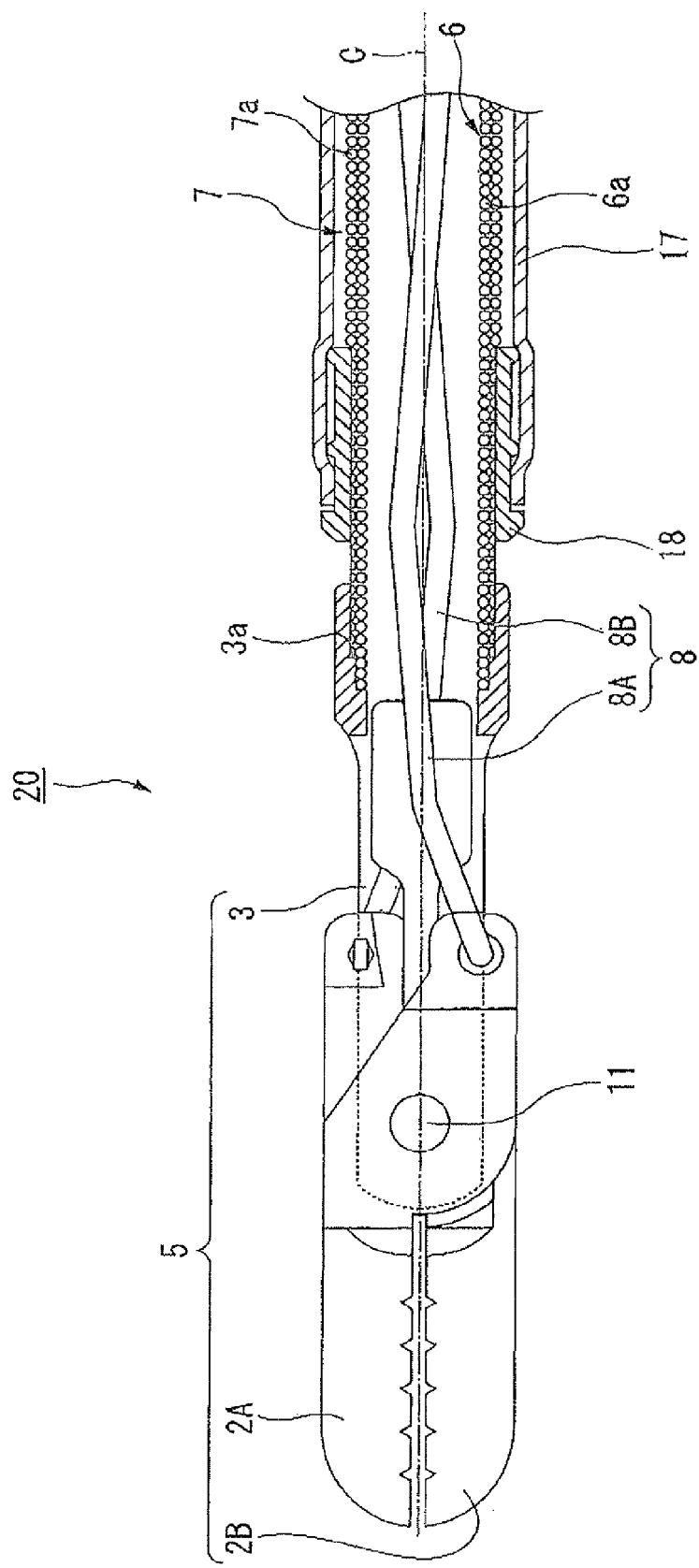
FIG. 5 is a cross sectional view showing a tip end side of forceps for an endoscope according to a second embodiment of the present invention.

Next is a description of a second embodiment with reference to FIG. 5.

Note that like constituent parts to those of the above first embodiment are designated with like reference numerals and are not repetitiously explained.

The difference between the second embodiment and the first embodiment lies in that a tip end of a first coil sheath 6 of forceps for an endoscope 20 according to the present embodiment is rotatably connected with a top cover 3 of a movable tip end portion 5 and that a base end thereof is rotatably connected with a protrusion portion 12B of an operation portion main unit 12 of an operation portion 10.

The operation of this forceps for an endoscope 20 will be described.

If the opening/closing direction of a pair of forceps arms 2A and 2B is different from the direction in which the affected area (not shown in the figure) is to be gripped, it is necessary to adjust the forceps for an endoscope 20 so that these two directions coincide. Therefore, as is the case with the first embodiment, an insulating tube 17 is gripped and the operation portion 10 is rotated about a central axis line C to make the opening/closing direction of the pair of forceps arms 2A and 2B coincide with the direction in which the affected area should be gripped.

At this time, when the operation portion 10 is rotated by a predetermined angle with respect to the insulating tube 17, a second coil sheath 7 follows the movable tip end portion 5 and the operation portion 10 to rotate by the predetermined angle about the central axis line C. On the other hand, the first coil sheath 6 does not follow the movable end tip portion 5 to rotate. Therefore, the second coil sheath 7 relatively rotates with respect to the first coil sheath 6.

After the opening/closing direction of the pair of forceps arms 2A and 2B is thus made to coincide with the direction in which the affected area should be gripped, the pair of forceps arms 2A and 2B is opened/closed by the same operation as the first embodiment.

According to this forceps for an endoscope 20, the first coil sheath 6 and the second coil sheath 7 rotate relatively to each other. Therefore, it is possible to favorably suppress discontinuous rotation resulting from a repetition of accumulation and release of distortion due to a difference in rotation angle between the two.

Figure 6:
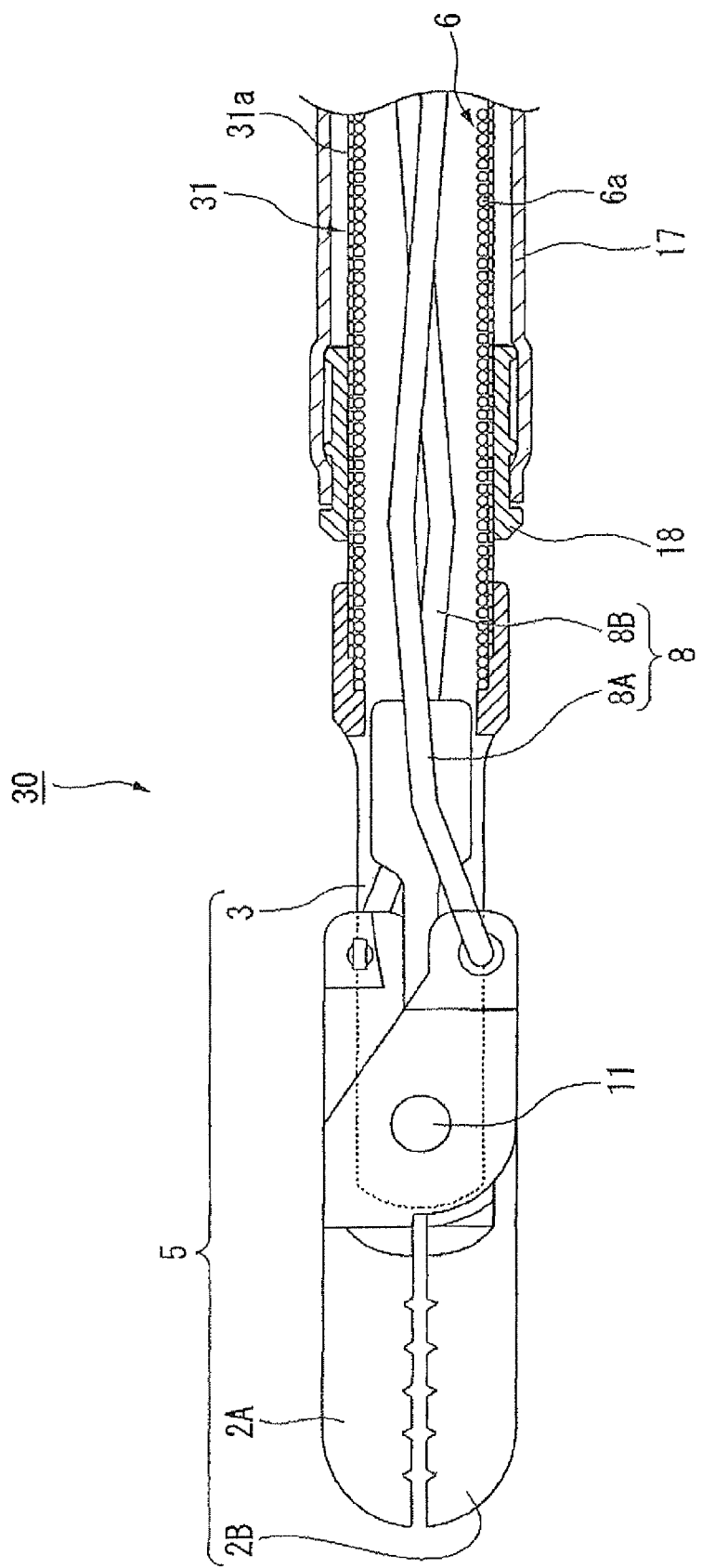
FIG. 6 is a cross sectional view showing a tip end side of forceps for an endoscope according to a third embodiment of the present invention.

Next is a description of a third embodiment with reference to FIG. 6.

Note that like constituent parts to those of the above embodiments are designated with like reference numerals and are not repetitiously explained.

The difference between the third embodiment and the first embodiment lies in that a wire 31a of a second coil sheath 31 of forceps for an endoscope 30 according to the present invention has a substantially rectangular cross section.

According to this forceps for an endoscope 30, the outer diameter of the second coil sheath 31 formed of wires 31a with a substantially rectangular cross section is made equal to the outer diameter of the second coil sheath 7 formed of wires 7a with a substantially circular cross section according to the first embodiment, and the wire 31a with a substantially rectangular cross section is adjusted in the width direction dimension and the height direction dimension. Thereby, it is possible to make the inner diameter of the second coil sheath 31 into which the wires 31a with a substantially rectangular cross section are wound smaller or larger than the inner diameter of the second coil sheath 7 into which the wires 7a with a substantially circular cross section are wound.

Moreover, when the diameters of the coil sheaths and the cross section area of the wires for both coil sheaths are made equal to each other, the wire 31a with a substantially rectangular cross section becomes larger than the wire 7a with a substantially circular cross section in the width direction dimension. Therefore, it is possible to increase the rigidity of the coil sheath.

Figure 7:
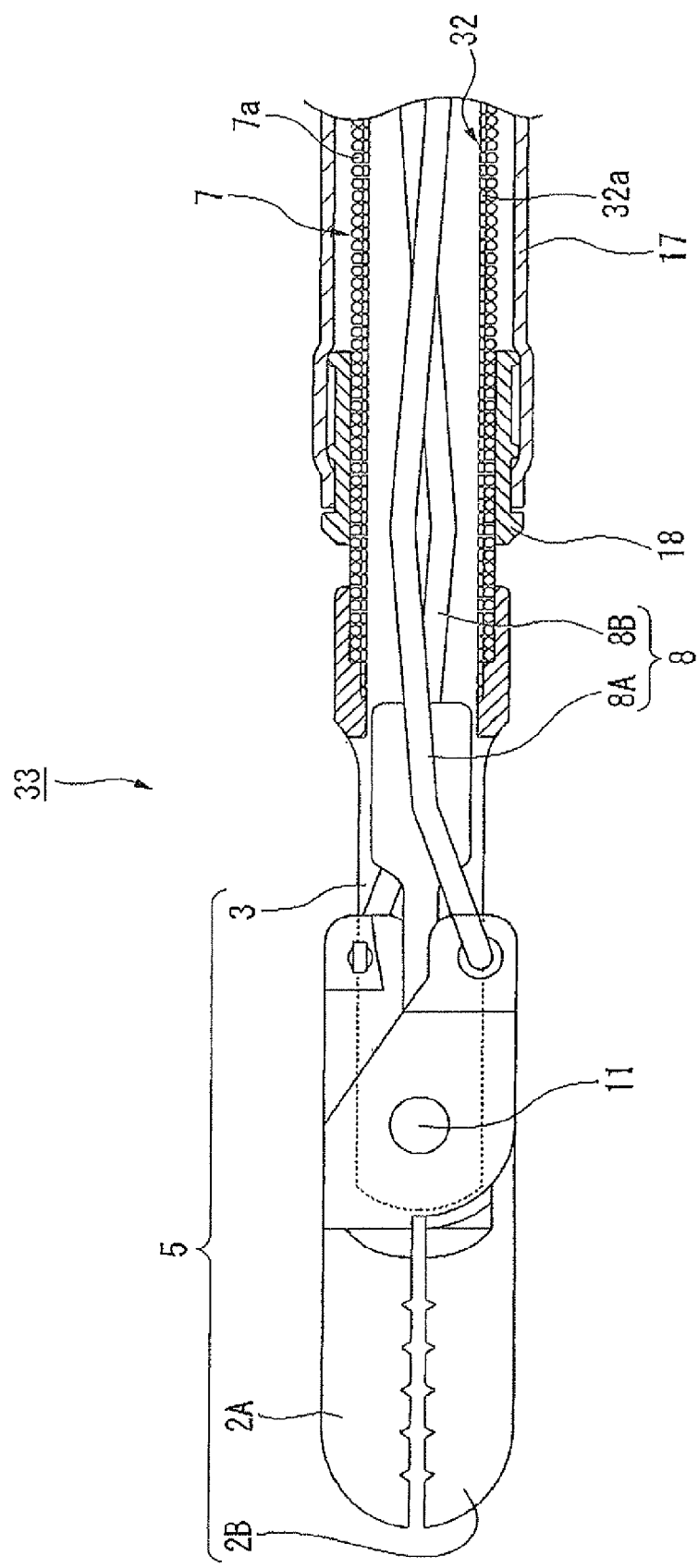
FIG. 7 is a cross sectional view showing a tip end side of a modification of the forceps for an endoscope according to the third embodiment of the present invention.
Figure 8:
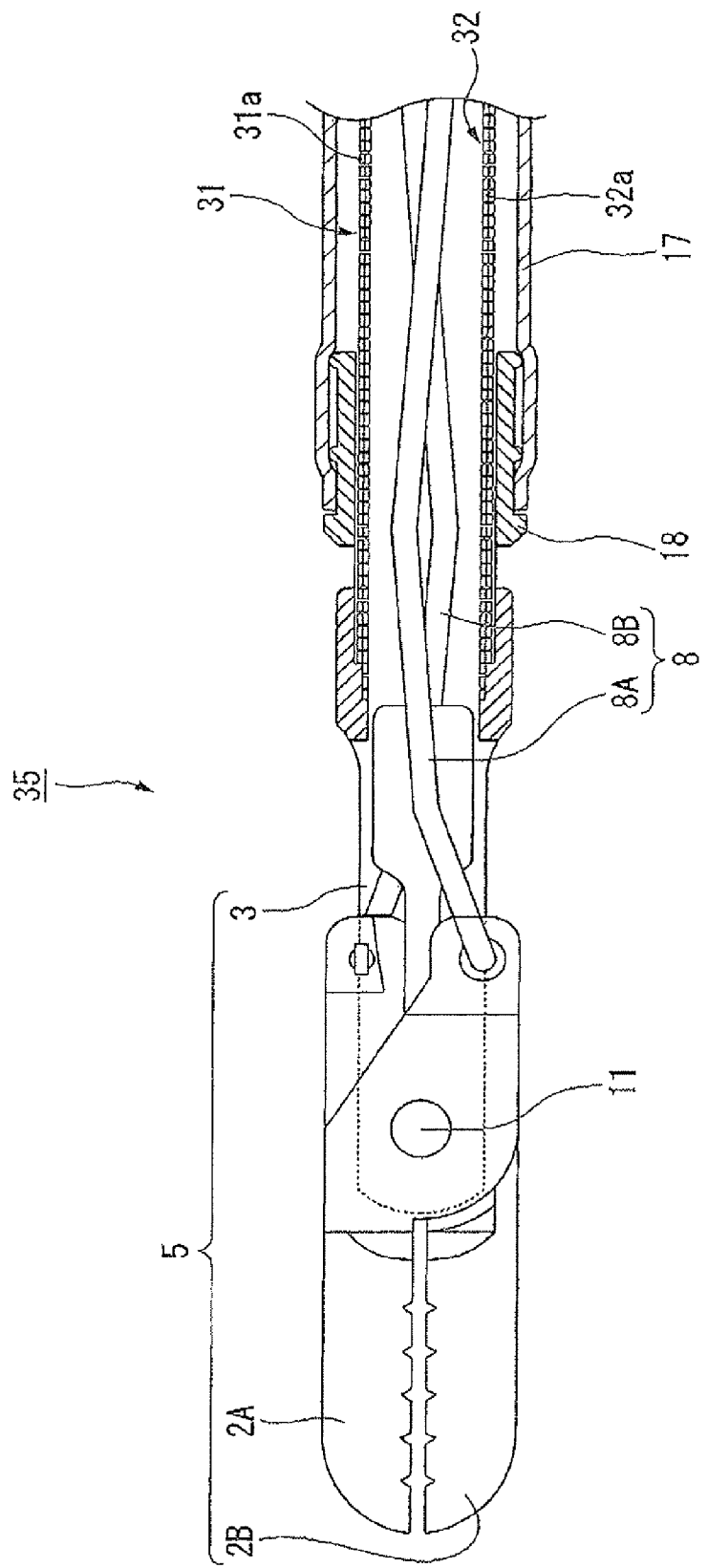
FIG. 8 is a cross sectional view showing a tip end side of a modification of the forceps for an endoscope according to the third embodiment of the present invention.

Note that forceps for an endoscope 33 as shown in FIG. 7 may be adopted in which not the wires 31a of the second coil sheath 31 but a wire 32a of a first coil sheath 32 has a substantially rectangular cross section. Furthermore, forceps for an endoscope 35 as shown in FIG. 8 may be adopted in which both a wire 32a of a first coil sheath 32 and wires 31a of a second coil sheath 31 have a substantially rectangular cross section. In both cases, an effect similar to that of the present embodiment is produced.

Figure 9:
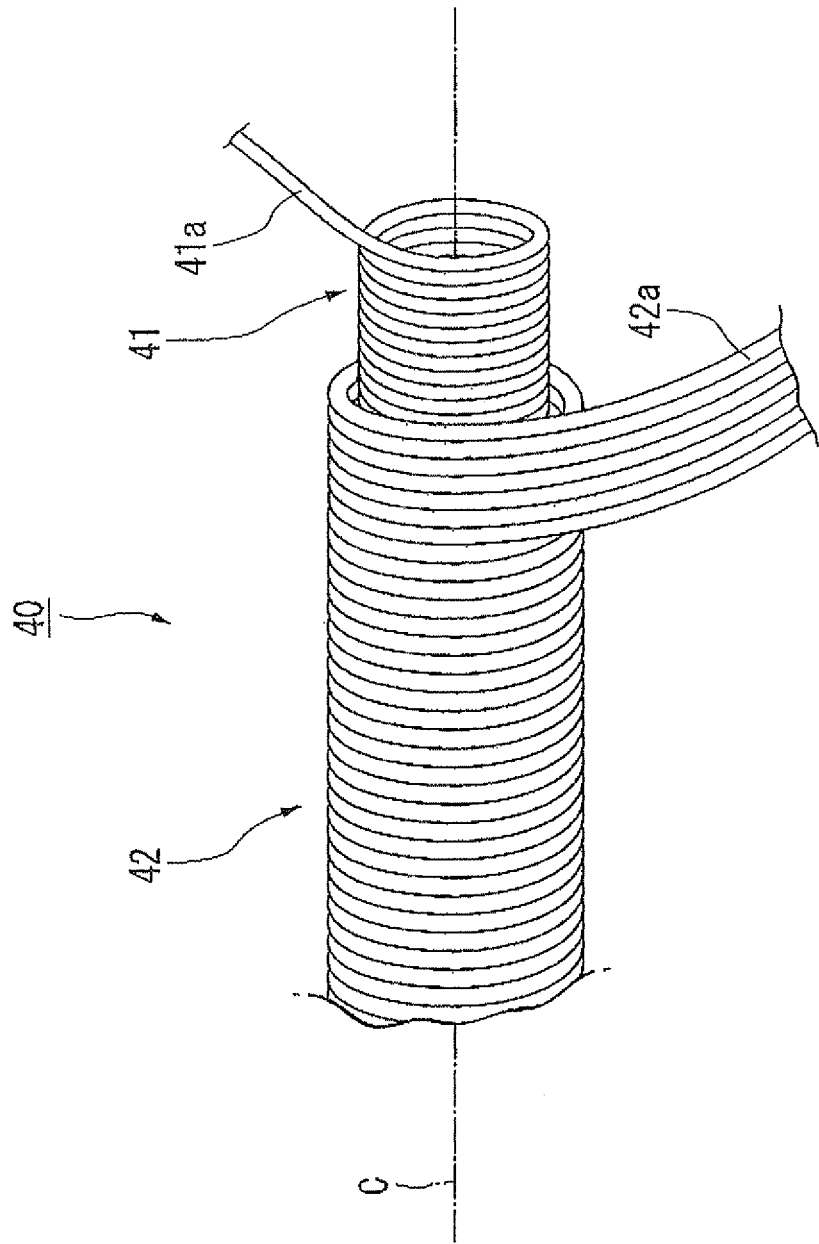
FIG. 9 is a schematic view showing a first coil sheath and second coil sheath of forceps for an endoscope according to a fourth embodiment of the present invention.

Next is a description of a fourth embodiment with reference to FIG. 9.

Note that like constituent parts to those of the above embodiments are designated with like reference numerals and are not repetitiously explained.

The difference between the fourth embodiment and the first embodiment lies in that the direction in which a wire 41a of a first coil sheath 41 of forceps for an endoscope 40 is wound and the direction in which wires 42a of a second coil sheath 42 are wound are opposite to each other with respect to a central axis line C.

That is, when the wire 41a of the first coil sheath 41 is wound counterclockwise with respect to the central axis line C, the wires 42a of the second coil sheath 42 are wound clockwise.

According to this forceps for an endoscope 40, even if the coil sheaths as a whole are rotated about their axis in either direction, a rotation force is loaded along the axis direction of the wire that is wound in a direction closer to the rotation direction. Therefore, it is possible to rotate the coil sheaths as a whole in a condition that they are little twisted.

Next is a description of a fifth embodiment with reference to the figures.

Note that like constituent parts to those of the above embodiments are designated with like reference numerals and are not repetitiously explained.

Figure 10:
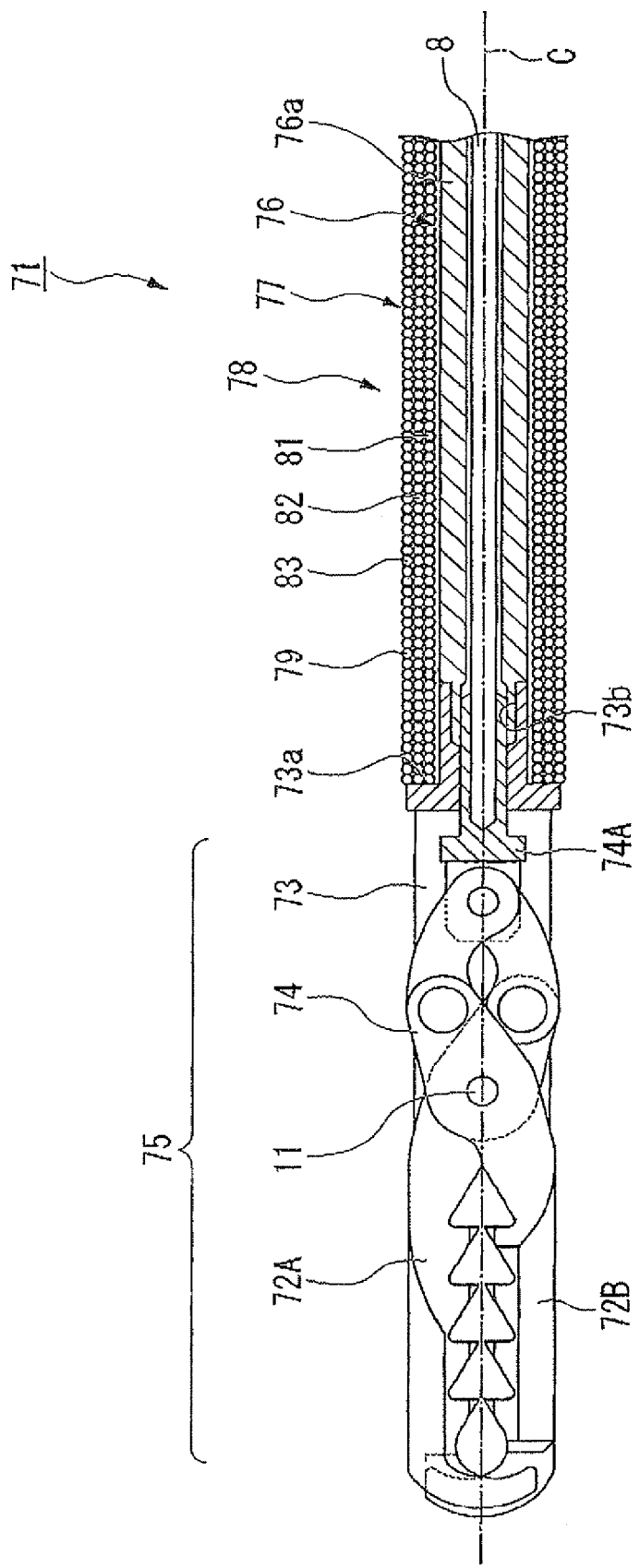
FIG. 10 is a cross sectional view showing a tip end side of forceps for an endoscope according to a fifth embodiment of the present invention.
Figure 11:
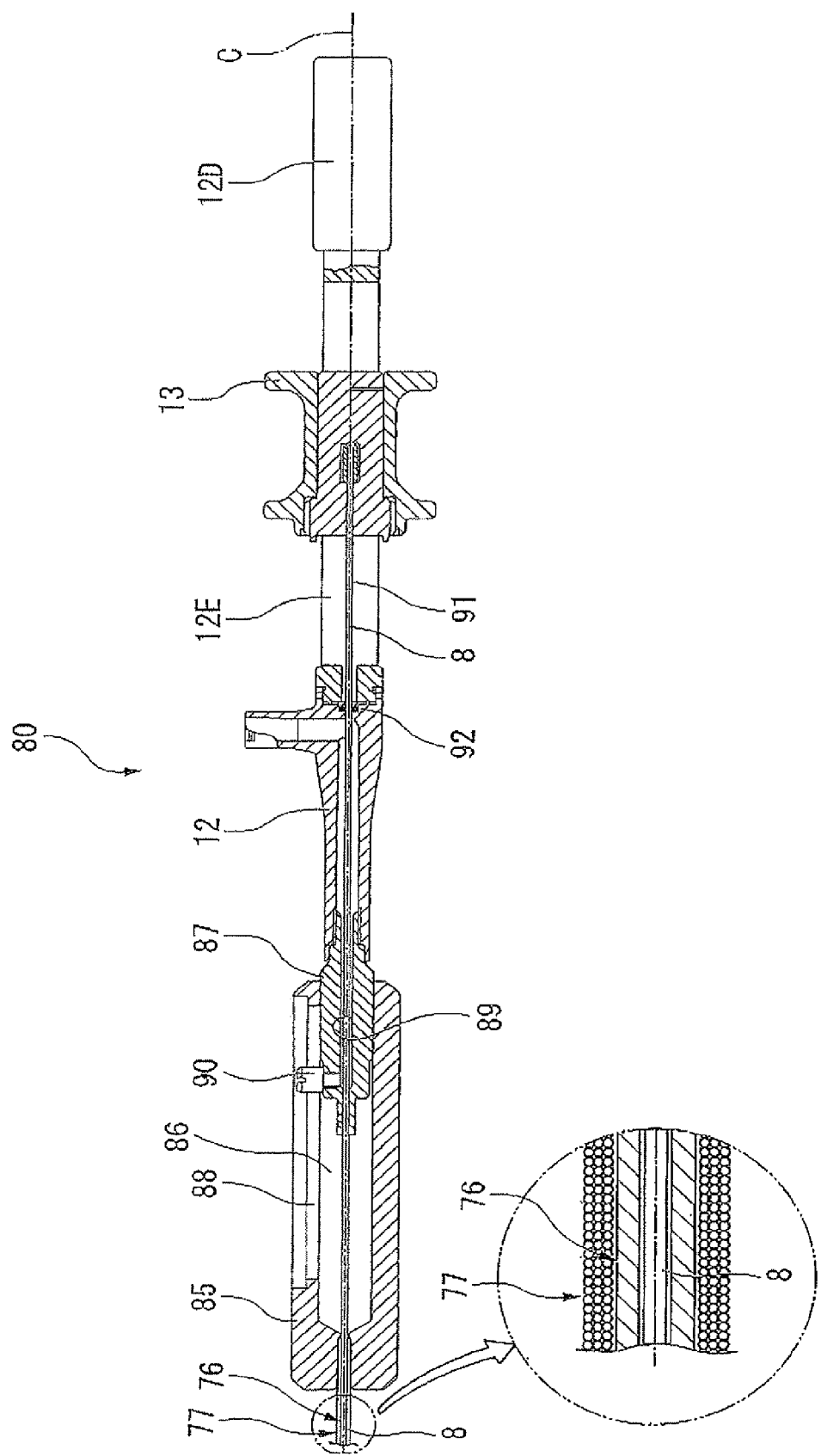
FIG. 11 is a cross sectional view showing an operation portion of forceps for an endoscope.

As shown in FIG. 10 and FIG. 11, forceps for an endoscope (a treatment tool for an endoscope) 71 includes: a movable tip end portion 75 that has a pair of forceps arms 72A and 72B and a tip end cover 73 for performing a treatment on a living body; a flat coil sheath 76 as a flexible first coil sheath into which a single flat plate 76a is densely wound in a spiral manner; a three-layered coil sheath 77 as a second coil sheath; an flexible operation wire 8 that is formed into an elongated thin shape, a tip end thereof being connected to the movable tip end portion 75, and the operation wire being movably inserted into the flat coil sheath 76; and an operation portion 80 for advancing and retracting the operation wire 8.

The tip end cover 73 is formed in a substantially cylindrical shape. On the tip end side thereof, there is provided a supporting pivot 11 for pivotally supporting the pair of forceps arms 72A and 72B as a movable portion. The pair of forceps arms 72A and 72B can be opened and closed by means of a link mechanism 74 through an advancing/retracting operation of the single operation wire 8. On an outer circumferential surface on a base end side of the tip end cover 73, there is provided a step 73a, to which a tip end side of the three-layered coil sheath 77 is fixed. On an inner circumferential surface on the base end side of the tip end cover 73, there is provided a step 73b, to which a tip end side of the flat coil sheath 76 is fixed. Between the tip end portion of the flat coil sheath 76 and a wire connection member 74A which connects the link mechanism 74 with the operation wire 8, there is provided a clearance in the axis line direction.

The flat coil sheath 76 that constitutes a long, flexible insertion portion 78 is made of a single wire. The flat plate 76a forms a coil sheath that comes in contact in the axis line direction in a surface contact manner. Therefore, the flat coil sheath 76 has a high resistance to compression or bending in the central axis line C direction. The flat plate 76a is made of, for example, stainless steel.

The three-layered coil sheath 77 is arranged substantially coaxially with the flat coil sheath 76 and the operation wire 8. It is made of three coil sheaths 81, 82, and 83 into which wires 79 are respectively wound, the coil sheaths being radially laminated. Adoption of the three-layered coil sheaths 81 to 83 facilitates transmission of the rotation torque about the axis line C. The wire 79 of the respective coil sheaths 81 to 83 is made of, for example, stainless steel. The wound directions of the respective wires are configured so that the wound directions of the radially neighboring coil sheaths are opposite to each other. As shown in FIG. 11, a base end of the three-layered coil sheath 77 is fixed to a rotation member 85.

The operation portion 80 has the rotation member 85 as a rotation operation portion into a tip end of which the three-layered coil sheath 77 is drawn and fixed. In the rotation member 85, there is bored a hole 86 that extends in the axis line C direction. A joint member 87 is inserted into this hole 86 from its base end side in a freely advancing and retracting manner. Moreover, on a side surface of the rotation member 85, there is formed in the longitudinal direction a slit 88 that penetrates from the outer circumference to the hole 86.

To joint member 87, the base end of the flat coil sheath 76 is fixed. The operation wire 8 extends through a hole 89 that is formed along the center of the joint member 87. Into the joint member 87, there is threaded a thread 90 in the radial direction from outside. The thread 90 has an outer diameter that allows insertion into the slit 88 of the rotation member 85. The thread 90 is a rotation restriction portion that serves as a guide for advancing and retracting the joint member 87, and also plays a role of a rotation stopper against the rotation member 85.

The joint member 87 is fixed to an operation portion main unit 12 by means of an insertion fit or the like. The operation portion main unit 12 is an advancing/retracting operation portion that has a ring 12D for hooking fingers and a slit 12E. A slide 13 is arranged in a freely advancing and retracting manner along the slit 12E. The operation wire 8 extends through the inside of the operation portion main unit 12, and is fixed to the slider 13 so as to be rotatable about the axis line C. To the slider 13, there is fixed a hard pipe 91. Insertion of the operation wire 8 into the pipe 91 prevents flexure of the operation wire 8 inside the slit 12E. The pipe 91 is partly drawn from the slit 12E into the inside of the operation portion main unit 12, and is slidably supported on the operation portion main unit 12 by means of an O-ring 92.

Next is a description of the operation of the forceps for an endoscope 71 according to the present embodiment.

If, when the forceps is inserted into an endoscope to perform a treatment in a body cavity, the opening/closing direction of the pair of forceps arms 72A and 72B is different from the direction in which the affected area is to be gripped, the forceps for an endoscope 71 is adjusted so as to match the directions.

When the operation portion 80, especially the rotation member 85, is rotated about the axis line C, rotation torque is transmitted to the three-layered coil sheath 77. Each of the three coil sheaths 81 to 83 that constitute the three-layered coil sheath 77 is relaxed or tightened depending on the direction in which it is wound.

For example, when the coil sheath 81 as the innermost layer and the coil sheath 83 as the outermost layer whose wound directions match are relaxed by the rotation and radially swollen, the coil sheath 82 as the intermediate layer is tightened and radially compressed. As a result, the coil sheath 81 as the innermost layer and the coil sheath 82 as the intermediate layer interfere with each other. The interference between the two radially neighboring coil sheaths 81 and 82 suppresses the radial swell and compression of the coil sheaths 81 and 82. Thereby, the rotation torque is transmitted to the movable tip end portion 75. On the other hand, when the coil sheath 81 as the innermost layer and the coil sheath 83 as the outermost layer whose wound directions match are tightened by the rotation, and the coil sheath 82 as the intermediate layer is relaxed, the coil sheath 82 as the intermediate layer and the coil sheath 83 as the outermost layer interfere with each other. Thereby, the rotation torque is transmitted to the movable tip end portion 75.

After the opening/closing direction of the pair of forceps arms 72A and 72B is matched with the direction in which to be gripped, the pair of the forceps arms 72A and 72B is opened and closed to perform a treatment. When the operation portion main unit 12 is gripped and the slider 13 is advanced, the operation wire 8 is advanced, to thereby open the pair of the forceps arms 72A and 72B that is coupled by means of the link mechanism 74.

Furthermore, when the slider 13 is advanced, the pair of the forceps arms 72A and 72B is closed to grip the tissue. At this time, when the operation wire 8 is forcefully pulled, such force as will pull the tip end cover 73 back to the proximal side is generated. This force works as force to compress the flat coil sheath 76. The flat coil sheath 76 is configured so that a flat plate 76a comes into contact in a surface contact manner, and hence has a high compression resistance. Therefore, the entirety of the insertion portion 78 is not significantly compressed or bent. The joint member 87 is inserted into the rotation member 85 in a freely advancing and retracting manner, and hence the compression force applied to the joint member 87 is not transmitted to the rotation member 85. Consequently, the compression force is not applied to three-layered coil sheath 77. Therefore, even in the condition that the operation wire 8 is forcefully pulled, the rotation following capability is maintained, allowing the movable tip end portion 75 to be rotated. Furthermore, even in the condition that the pair of the forceps arms 72A and 72B is opened, the rotation following capability is maintained, allowing the movable tip end portion 75 to be rotated.

According to the forceps for an endoscope 71, it is configured such that the flat coil sheath 76 has rigidity against bending and resistance to a compression force and that rotation torque is transmissible by the three-layered coil sheath 77. Therefore, when the forceps is inserted into an endoscope to perform a treatment, it is possible to improve both the rotation operability and workability of the movable tip end portion 75 and to facilitate a manipulation.

Figure 12:
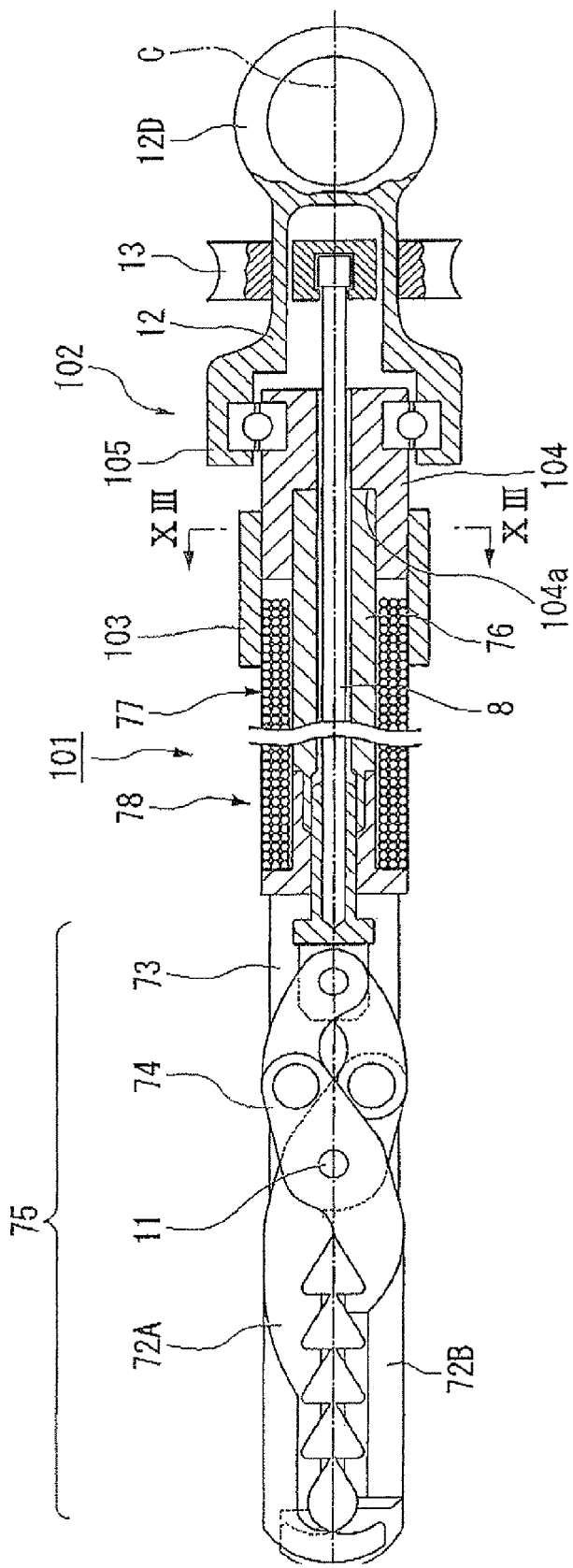
FIG. 12 is a cross sectional view showing a construction of forceps for an endoscope according to a sixth embodiment of the present invention.
Figure 13:
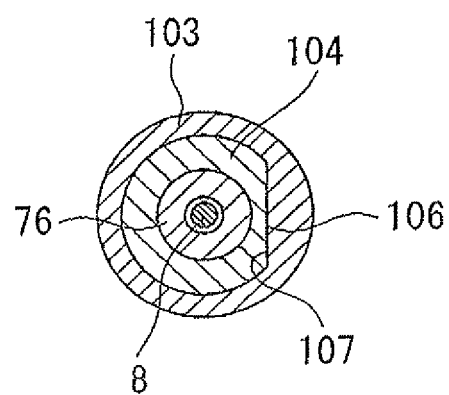
FIG. 13 is a cross sectional view taken along the line XIII-XIII in FIG. 12.

Next is a description of a sixth embodiment with reference to FIG. 12 and FIG. 13.

Note that like constituent parts to those of the above embodiments are designated with like reference numerals and are not repetitiously explained. The difference between the sixth embodiment and the fifth embodiment lies in the construction of the operation portion.

As shown in FIG. 12, the operation portion 102 has a rotation ring 103 as a rotation operation portion, in which a base end of a three-layered coil sheath 77 is fixed to an inner circumferential surface thereof. On the inner side of the rotation ring 103, there is arranged a joint member 104 in a relatively unrotatable manner. To the joint member 104, there is rotatably mounted an operation portion main unit 12 via a bearing 105.

The joint member 104 has a substantially cylindrical shape. A flat coil sheath 76 is abutted and fixed to a step portion 104a in an inner circumference of the joint member 104. Between a tip end surface of the joint member 104 and the three-layered coil sheath 77, there is formed a clearance. This clearance prevents the axial force that has acted on the joint member 104 from being directly transmitted to the three-layered coil sheath 77.

As shown in FIG. 13, an outer circumference of the joint member 104 is formed to have a D-shaped cross section by cutting a part of the cylinder along a plane 106. To fit with this plane 106, there is provided a plane 107 on an inner surface of the rotation ring 103. In this manner, rotation restriction portion is made of the planes 106 and 107 which are asymmetrical in the rotation direction, to thereby make the rotation ring 103 and the joint member 104 relatively movable but relatively unrotatable in the axis line C direction.

The bearing 105 is press-fitted and fixed into an outer circumference on a base end side of the joint member 104. Onto an outer circumference of the beating 105, an inner circumferential surface of the operation portion main unit 12 is press-fitted and fixed. In the operation portion main unit 12, an operation wire 8 that extends through the joint member 104 is fixed to a slider 13 in a manner rotatable about the axis line C.

For the forceps for an endoscope 101, when the orientation of the pair of the forceps arms 72A and 72B is adjusted, the operation portion main unit 12 is fixed and the rotation ring 103 is rotated. The rotation torque is transmitted to the joint member 104 and the three-layered coil sheath 77 that is fixed to the rotation ring 103. As a result, the pair of the forceps arms 72A and 72B together with the movable tip end portion 75 are rotated about the axis line.

When a compression force in the axis line C direction is applied, such as when the slider 13 is operated to open/close the pair of forceps arms 72A and 72B, the compression force acts on the operation portion main unit 12 and the joint member 104 that is coupled thereto via the bearing 105. Then, the compression force is received by the flat coil sheath 76 that is fixed to the joint member 104. The rotation ring 103 is able to advance and retract with respect to the joint member 104, to thereby prevent the compression force from being transmitted. Therefore, the compression force does not act on the three-layered coil sheath 77.

In the forceps for an endoscope 101, the joint member 104 whose cross section is cut into a D-shape is engaged with the rotation ring 103 only in the rotation direction, to thereby prevent a compression force from being transmitted to the three-layered coil sheath 77. As a result, an advantage similar to that as mentioned above is obtained.

By coupling the joint member 104 and the operation portion main unit 12 by means of the bearing 105, it is possible to adjust the orientation of the pair of forceps arms 72A and 72B in a state with the operation portion main unit 12 being fixed. Note that the joint member 104 and the operation portion main unit 12 may be fixed to each other without providing the bearing 105. When the orientation of the pair of forceps arms 72A and 72B is adjusted, the rotation ring 103 is rotated together with the operation portion main unit 12.

Figure 14:
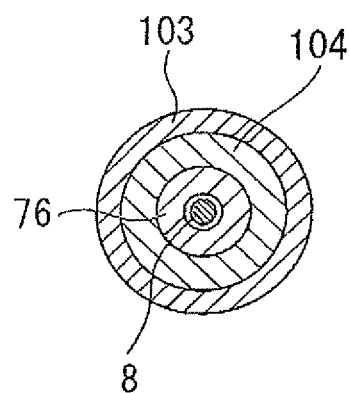
FIG. 14 is a cross sectional view taken along the line XIII-XIII in FIG. 12 and showing forceps for an endoscope according to a seventh embodiment of the present invention.

Next is a description of a seventh embodiment with reference to FIG. 12 and FIG. 14.

Note that like constituent parts to those of the above embodiments are designated with like reference numerals and are not repetitiously explained. The difference between the seventh embodiment and the sixth embodiment lies in the construction of the operation portion.

As shown in FIG. 14, a joint member 104 of an operation portion 102 has a cylindrical shape, and is arranged so as to be relatively rotatable with respect to a rotation ring 103. When the orientation of a pair of forceps arms 72A and 72B is adjusted, a rotation ring 103 is gripped and rotated. Rotation torque is transmitted to a tip end side via a three-layered coil sheath 77. When a compression force is applied to a flat coil sheath 76, such as when the pair of forceps arms 72A and 72B is opened/closed, the compression force is not transmitted to the three-layered coil sheath 77 because the rotation ring 103 is not engaged with the joint member 104.

In this embodiment, an advantage similar to that in the above-mentioned embodiments is obtained with the construction that allows the rotation ring 103 and the joint member 104 to relatively rotate.

In a condition that a compression force is applied to the flat coil sheath 76, the flat coil sheath 76 becomes stiff. Consequently, it requires a huge amount of energy to rotate the whole length of the flat coil sheath 76. However, with the construction of this embodiment, it is possible to rotate a movable tip end portion 75 by only a tip end and its adjacent section of the flat coil sheath 76 being twisted with rotation force that is transmitted by the three-layered coil sheath 77. Under a certain condition, rotatability improves.

In the forceps for an endoscope 71 as shown in FIG. 10 and FIG. 11, it is possible to make the rotation member 85 and the joint member 87 relatively rotatable if it is constructed without the thread 90. Also in this case, a similar working effect is obtained.

Figure 15:
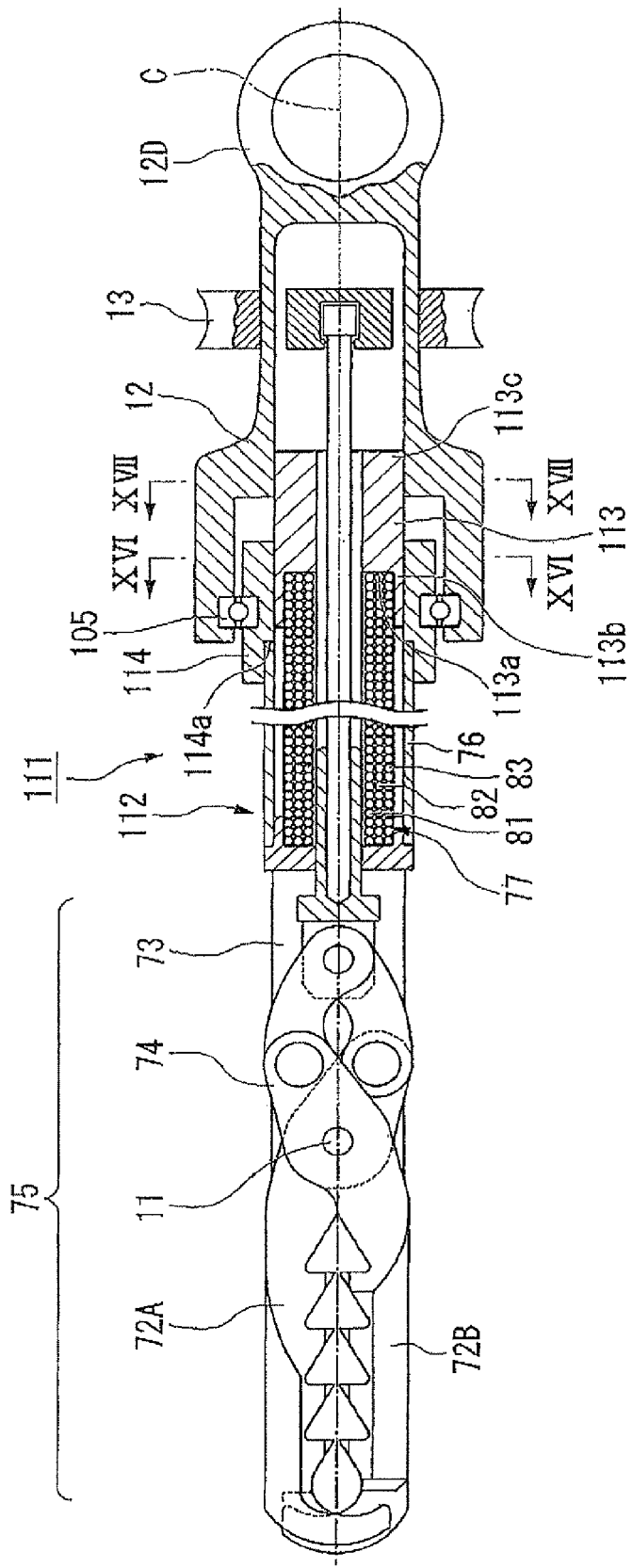
FIG. 15 is a cross sectional view showing a construction of forceps for an endoscope according to an eighth embodiment of the present invention.
Figure 16:
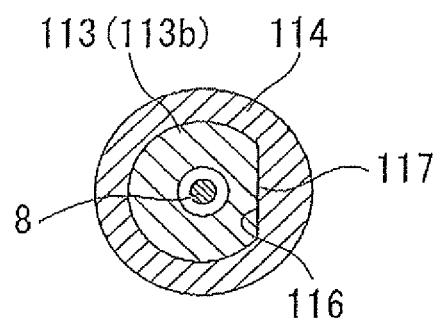
FIG. 16 is a cross sectional view taken along the line XVI-XVI in FIG. 15.

Next is a description of an eighth embodiment with reference to FIG. 15 and FIG. 16.

Note that like constituent parts to those of the above embodiments are designated with like reference numerals and are not repetitiously explained.

As shown in FIG. 15, in an insertion portion 112 of forceps for an endoscope 111, there are coaxially arranged an operation wire 8, a three-layered coil sheath 77, and a flat coil sheath 76 in the order from inside in the radial direction. Both the three-layered coil sheath 77 and the flat coil sheath 76 are fixed to a tip end cover 73 of a movable tip end portion 75.

A base end side of the three-layered coil sheath 77 is abutted and fixed to a step 113a that is formed in an inner circumference of a rotation ring 113 as a cylindrical rotation operation portion. As shown in FIG. 16, an outer circumference of a tip end portion 113b of the rotation ring 113 is formed to have a D-shaped cross section by cutting a part of the circle along a plane 117. An outline of a base end portion 113c of the rotation ring 113 is circular.

On the outside of the rotation ring 113, there is arranged a joint member 114. The joint member 114 has a cylindrical shape. To a step 114a on a tip end side of the joint member 114, there is fixed a base end of the flat coil sheath 76. On an inner circumferential side of the rotation ring 113, there is formed a plane 116 to fit with the plane 117 of the rotation ring 113. As a result, the joint member 114 and the rotation ring 113 are unable to relatively rotate, but are slidable in the axis line C direction. Into an outer circumference of the joint member 114, a bearing 105 is press-fitted and fixed.

The bearing 105 is also press-fitted into an inner circumferential portion of an operation portion main unit 12. Therefore, it is possible to rotate the joint member 114 and the rotation ring 113 with respect to the operation portion main unit 12.

When the orientation of a pair of forceps arms 72A and 72B is adjusted, the operation portion main unit 12 is gripped and the joint member 114 is rotated. When the joint member 114 is rotated, the three-layered coil sheath 77 is rotated via the rotation ring 113 that is engaged with the joint member 114 in the rotation direction by means of a rotation restriction portion made of the planes 116 and 117. As a result, the rotation torque is transmitted to the movable tip end portion 75 by the three-layered coil sheath 77. Thereby, the orientation of the pair of forceps arms 72A and 72B is adjusted. Note that rotation of the joint member 114 causes the flat coil sheath 76 arranged as an outermost layer to rotate accordingly.

When a compression force in the axis line C direction is generated in opening/closing the pair of forceps arms 72A and 72B, the compression force is received by the flat coil sheath 76 arranged on the outside. Because the joint member 114 does not engage with the rotation ring 113 in the axis line C direction, the compression force does not act on the three-layered coil sheath 77. As a result, even while the compression force is working, the rotation torque is transmitted by the three-layered coil sheath 77 without being decreased.

In this embodiment, an advantage similar to that as mentioned above is obtained. The flat coil sheath 76 has a larger outer diameter compared with that of the sixth embodiment. Therefore, the insertion portion 112 has increased rigidity against bending. It also has increased flexural rigidity when the operation wire 8 is pulled.

Here, a modification of this embodiment will be described.

Figure 17:
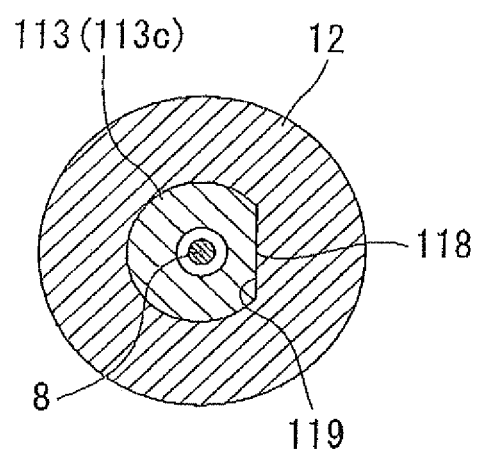
FIG. 17 is a cross sectional view taken along the line XVII-XVII in FIG. 15.

In the forceps for an endoscope 111 as shown in FIG. 15, it may be configured such that the outer circumference of the rotation ring 113 is made circular to prevent the rotation ring 113 and the joint member 114 from engaging with each other also in the rotation direction. In this case, the rotation ring 113 and the operation portion main unit 12 are coupled relatively unrotatably and slidably in the axis line C direction. As the cross section is shown in FIG. 17, a D-shaped cross section by the plane 118 is formed only in the outer circumference of the base end portion 113c of the rotation ring 113, and a plane 119 which engages with the plane 118 is provided on an inner circumference side of the operation portion main unit 12.

When the orientation of the pair of forceps arms 72A and 72B is adjusted, the operation portion main unit 12 is rotated. With the rotation of the rotation ring 113 that is engaged with the operation portion main unit 12 in the rotation direction by means of the rotation restriction portion made of the planes 118 and 119, the three-layered coil sheath 77 is accordingly rotated. The rotation torque is transmitted to the movable tip end portion 75 by the three-layered coil sheath 77. Thereby, the orientation of the pair of forceps arms 72A and 72B is adjusted.

When a compression force in the axis line C direction is generated in opening/closing the pair of forceps arms 72A and 72B, the compression force is received by the flat coil sheath 76 arranged on the outside. The joint member 114 is not engaged with the rotation ring 113. Therefore, even while the compression force is working, it is possible for the rotation torque to be transmitted by the three-layered coil sheath 77.

Figure 18:
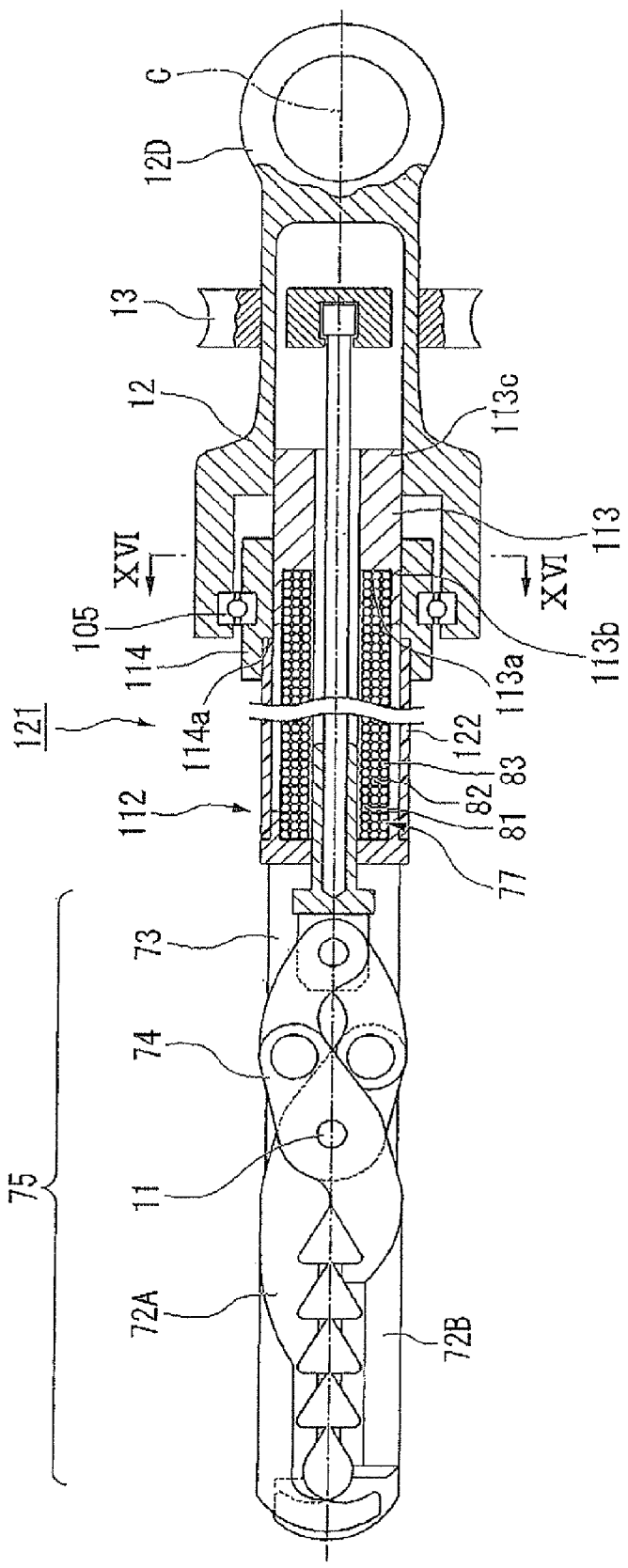
FIG. 18 is a cross sectional view showing a construction of forceps for an endoscope according to a ninth embodiment of the present invention.

Next is a description of an endoscope 121 according to a ninth embodiment with reference mainly to FIG. 18.

Note that like constituent parts to those of the above embodiments are designated with like reference numerals and are not repetitiously explained. This embodiment is characterized by including a coated tube instead of the flat coil sheath of the eighth embodiment.

A coated tube 122 is arranged outside a three-layered coil sheath 77, and the ends thereof are fixed to a tip end cover 73 and a joint member 114, respectively. As the material for the coated tube 122, for example PEEK (polyether ether ketone resin), PTFE (polytetrafluroethelene resin), POM (polyacetal), FEP (tetrafluoroethylene-hexafluoropropylene copolymer), PFA (tetrafluoroethylene-perfluoroalkylvinylether copolymer resin), or the like can be used.

When the orientation of a pair of forceps arms 72A and 72B is adjusted, the operation portion main unit 12 is gripped and the joint member 114 is rotated. When the joint member 114 is rotated, the three-layered coil sheath 77 is rotated via the rotation ring 113 that is engaged with the joint member 114 in the rotation direction. As a result, the rotation torque is transmitted to the movable tip end portion 75 by the three-layered coil sheath 77. Thereby, the orientation of the pair of forceps arms 72A and 72B is adjusted. Note that rotation of the joint member 114 causes the coated tube 122 to rotate accordingly.

When a compression force in the axis line C direction is generated in opening/closing the pair of forceps arms 72A and 72B, the compression force is received by the coated tube 122 arranged on the outside. The joint member 114 does not engage with the rotation ring 113 in the axis line C direction. Consequently, the compression force does not act on the three-layered coil sheath 77. Therefore, even while the compression force is working, it is possible for the rotation torque to be transmitted by the three-layered coil sheath 77. Furthermore, also when pulling force in the axis line C direction is generated, it is possible for the pulling force to be received by the coated tube 122.

In this embodiment, an advantage similar to that as mentioned above is obtained. The outermost layer of the insertion portion 112 is the coated tube 122. Therefore, insulation is possible without changing the diameter of the insertion portion 112.

Figure 19:
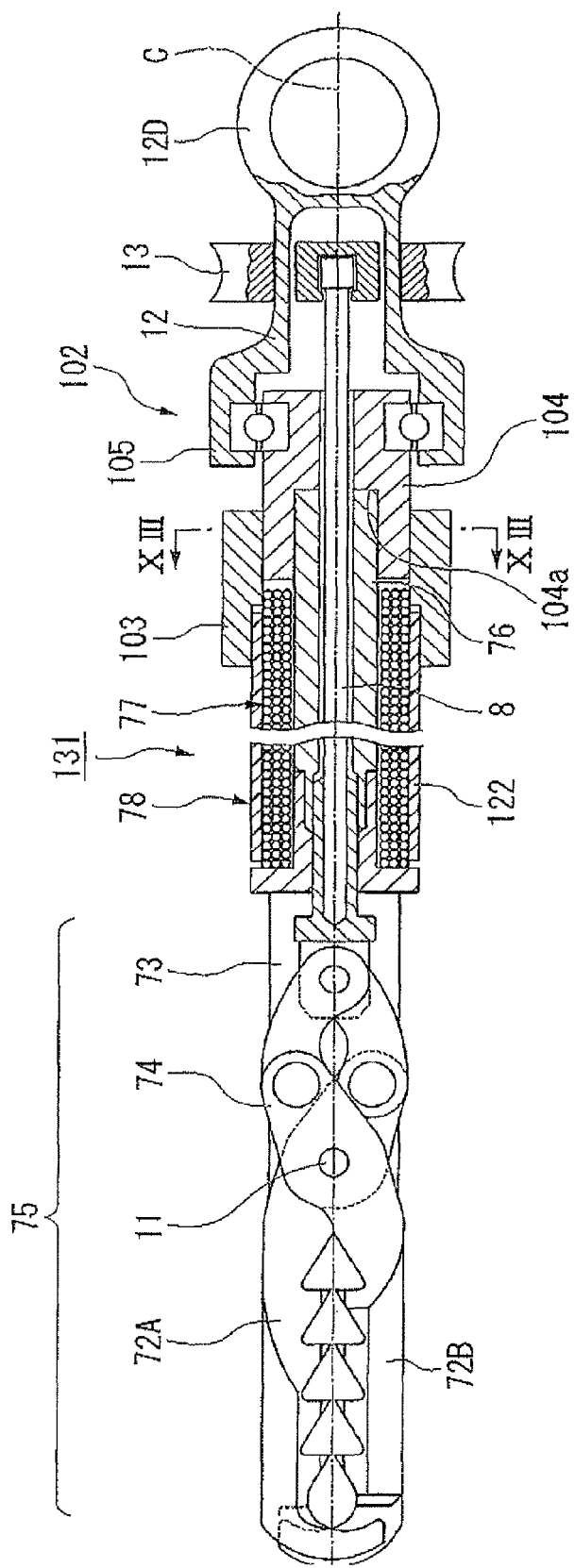
FIG. 19 is a cross sectional view showing a construction of forceps for an endoscope according to a tenth embodiment of the present invention.
Figure 20:
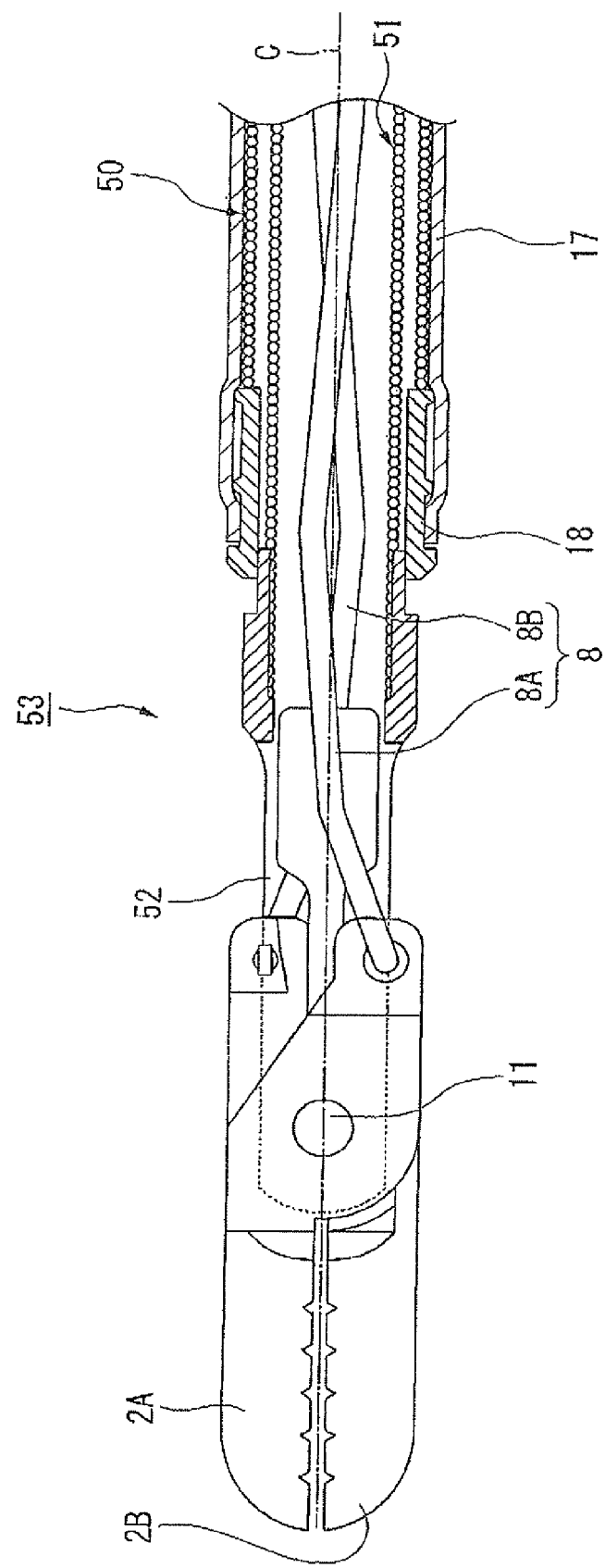
FIG. 20 is a cross sectional view showing a tip end of a modification of the forceps for an endoscope according to the first embodiment of the present invention.

Next is a description of an endoscope 131 according to a tenth embodiment with reference mainly to FIG. 19.

Note that like constituent parts to those of the above embodiments are designated with like reference numerals and are not repetitiously explained. This embodiment is characterized by further including a coated tube as the outermost layer of the insertion portion of the sixth embodiment.

A coated tube 122 is arranged outside a three-layered coil sheath 77, and both ends thereof in the axis line C direction have a clearance respectively to a tip end cover 73 and a rotation ring 103. Note that the coated tube 122 may be fixed to both the tip end cover 73 and the rotation ring 103, or fixed to only one of them.

Operations in the rotation manipulation and the opening/closing manipulation are similar to those of the sixth embodiment. When the coated tube 122 is fixed to the rotation ring 103, the coated tube 122 is also rotated together with the three-layered coil sheath 77. Moreover, it is possible for the compression force to be received not only by a flat coil sheath 76 but also by the coated tube 122.

In this embodiment, an advantage similar to that as mentioned above is obtained. Addition of the coated tube 122 as the outermost layer of the insertion portion 78 enables insulation of the insertion portion 78, and also enhances compression resistance and flexural rigidity.

Here, in the fifth to tenth embodiments, a two-layered coil sheath may be used instead of the three-layered coil sheath 77. A two-layered coil sheath is one in which two coil sheaths are coaxially arranged. In this case, while maintaining the inner and outer diameters the same as those of the three-layered coil sheath 77, it is possible to make the diameter of a wire of a coil larger and to increase rotational force in a certain direction.

In the fifth to tenth embodiments, even if it is configured such that the three-layered coil sheath 77 receives axis force such as a compression force and a pulling force in the axis line C direction, at least either the flat coil sheath 76 or the coated tube 122 is excellent in compression resistance. Therefore, the three-layered coil sheath 77 will not be compressed or pulled so strongly as to prevent the transmission of the rotation torque. At this time, each of the coil sheaths 81 to 83 may be previously extended a little in the axis line C1 direction so that it becomes densely wound when a compression force in the axis line direction is applied. Such construction leads to a simpler construction, which makes it possible to suppress manufacturing cost.

The technical scope of the present invention is not limited to the above-mentioned embodiments and various modifications can be made as long as they do not depart from the spirit or scope of this invention.

For example, in the above embodiments, the first coil sheath 6 is arranged inside the second coil sheath 7 or 31. However, the invention is not limited to this. As shown in FIG. 10, forceps for an endoscope 53 may be adopted in which a second coil sheath 51 is rotatably arranged inside a first coil sheath 50 onto whose outer surface is fitted an insulating tube 17, only a tip end of the second coil sheath 51 is fixed to a tip end cover 52, and an operation wire 8 is arranged in a freely advancing and retracting manner with respect to the second coil sheath 51.

In this case, when the insulating tube 17 is gripped and an operation portion (not shown in the figure) is rotated about a central axis line C, the second coil sheath 51 is rotated with respect to the first coil sheath 50. At this time, because the inner circumferential surface of the first coil sheath 50 and the outer circumferential surface of the second coil sheath 51 are made of stainless steel, it is possible to keep the frictional force produced by the relative rotation low, enabling smooth rotation.

Furthermore, in the above embodiments, the contact surfaces between the first coil sheath and the second coil sheath may be partly adhered by laser welding or the like. In this case, the coil sheaths that overlap each other in the radial direction rotate integrally, preventing distortion from being accumulated or released from between the sheaths. Therefore, it is possible to smoothly rotate the coil sheaths.

In this invention, even if a compression force is loaded on the second coil sheath whose tip end and base end are fixed when advancing/retracting operation is performed on the operation portion to move the operation wire in the axis direction with respect to the first coil sheath in order to operate the movable tip end portion, compression on the second coil sheath is relaxed by the first coil sheath with high compression resistance due to a single wire spirally wound, thereby allowing a sufficient control force to be favorably transmitted to the movable tip end portion. Moreover, the second coil sheath with high rotation transmissibility due to a plurality of wires spirally wound in the same direction is less likely to be twisted than the first coil sheath. Therefore, even if the first sheath is going to be twisted when the operation portion is rotated about the axis to rotate the movable tip end portion, it is possible to obtain high rotation following capability. In addition, because the outer diameter of the second coil sheath is larger than that of the first coil sheath, it is possible to make the transmissibility of the rotation torque in the second coil sheath higher.

The first coil sheath is rotatably arranged to the second coil sheath. Consequently, even if the second coil sheath is twisted when the movable tip end portion is intended to be rotated by rotating the operation portion about the central axis line of the coil sheath, it is possible to prevent at least the first coil sheath from being twisted. As a result, it is possible to maintain high rotation transmissibility.

Even if the wires of a coil sheath formed of a wire with a substantially circular cross section and a coil sheath formed of a wire with a substantially rectangular cross section are equal in cross section area, or the two coil sheaths are equal in outer or inner diameter, it is possible to change the diameter of the coil sheath formed of the wire with a substantially rectangular cross section by adjusting the wire with a substantially rectangular cross section in the width direction dimension and the height direction dimension. For example, it is possible to make the outer diameter of a coil sheath into which a wire with a substantially rectangular cross section is wound smaller than the outer diameter of a coil sheath into which a wire with a substantially circular cross section is wound, or to make the inner diameter of a coil sheath into which a wire with a substantially rectangular cross section is wound larger than the inner diameter of a coil sheath into which a wire with a substantially circular cross section is wound.

When the winding directions of the wires coincide with the rotation direction of the coil sheaths as a whole about their axis, a rotation force is loaded on the coil sheaths along the axis of the wires. Therefore, it is possible to rotate the coil sheaths with little twist.

Even if the coils sheaths as a whole are rotated about their axis in either direction, a rotation force is loaded along the winding direction of the wire that is wound in a direction closer to the rotation direction. Therefore, it is possible to rotate the coil sheaths with little twist.

When operation is performed on the advancing/retracting operation portion to advance and retract the operation wire in the axis direction with respect to the first sheath, the first sheath receives the axial force such as compressive force and tensile force. Therefore, it is possible to prevent the second sheath from losing the function of the rotation by being compressed or pulled too much. Consequently, when the rotation operation portion is rotated, the rotation torque is transmitted to the movable tip end portion through the second sheath.

According to the present invention, it is possible to improve both the rotation operability and workability of the movable tip end portion and to facilitate a manipulation.

While preferred embodiments of the invention have been described and illustrated above, it should be understood that these are exemplary of the invention and are not to be considered as limiting. Additions, omissions, substitutions, and other modifications can be made without departing from the spirit or scope of the invention. The invention is not to be considered as limited by the foregoing description and is only limited by the scope of the appended claims.

What is claimed is:

1. A treatment tool of an endoscope comprising:
    a movable tip end portion having a movable part that performs a treatment on a living body;
    a flexible operation wire that is formed into an elongated shape, a distal end of the flexible operation wire being connected to the movable tip end portion;
    an advancing/retracting operation portion for advancing and retracting the operation wire in an axis direction;
    an inner sheath that is coaxial with the flexible operation wire, a distal end of the inner sheath being fixed to the movable tip end portion, and a proximal end of the inner sheath being fixed to the advancing/retracting operation portion;
    an outer sheath that is coaxial with the flexible operation wire and the inner sheath, a distal end of the outer sheath being fixed to the movable tip end portion;
    a rotation member to which a proximal end of the outer sheath is fixed, the rotation member being rotatably movable about the axis direction wherein
    the inner sheath receives an axial force generated between the movable tip end portion and the advancing/retracting operation portion in the axis direction when the operation wire is advanced or retracted by operating the advancing/retracting operation portion, and
    the rotation member is further configured to translate in the axis direction such that a relative displacement between the advancing/retracting operation portion having the proximal end of the inner sheath and the rotation member having the proximal end of the outer sheath in the axis direction is generated and transmittance of the axial force to the outer sheath is at least diminished.

2. The treatment tool of an endoscope according to claim 1, wherein the rotation member is fixed relative to the advancing/retracting operation portion about an axis of the operation wire so as to rotate together.

3. The treatment tool of an endoscope according to claim 1, wherein the rotation member is rotatable relative to the advancing/retracting operation portion about an axis of the operation wire.

4. The treatment tool of an endoscope according to claim 1, wherein the inner sheath is a tube.

5. The treatment tool of an endoscope according to claim 1, wherein the inner sheath is a coil sheath.

6. The treatment tool of an endoscope according to claim 5, wherein
    the inner sheath is a coil sheath that has a higher compression resistance than the outer sheath, and
    the outer sheath is a coil sheath that has a higher rotation-following capability than the inner sheath.

7. The treatment tool of an endoscope according to claim 1, wherein a gap is formed between the proximal end of the outer shaft and a distal end of the advancing/retracting operation portion in the axis direction.

* * * * *